(12) United States Patent
von Andrian et al.

(10) Patent No.: US 7,825,088 B2
(45) Date of Patent: Nov. 2, 2010

(54) METHODS FOR THE TREATMENT OF MULTIPLE MYELOMA

(75) Inventors: Ulrich H. von Andrian, Brookline, MA (US); Irina Mazo, Chestnut Hill, MA (US); Jean-Marc Gauguet, Boston, MA (US)

(73) Assignee: The CBR Institute for Biomedical Research, Inc., Boston, MA (US)

( * ) Notice: Subject to any disclaimer, the term of this patent is extended or adjusted under 35 U.S.C. 154(b) by 51 days.

(21) Appl. No.: 11/409,927

(22) Filed: Apr. 24, 2006

(65) Prior Publication Data

US 2007/0003558 A1 Jan. 4, 2007

Related U.S. Application Data

(60) Provisional application No. 60/674,463, filed on Apr. 25, 2005.

(51) Int. Cl.
*A61K 38/12* (2006.01)
*A61K 39/395* (2006.01)
(52) U.S. Cl. ..................................... 514/11
(58) Field of Classification Search .................... 514/11
See application file for complete search history.

(56) References Cited

U.S. PATENT DOCUMENTS

| 6,825,351 | B2 | 11/2004 | McEachern et al. | |
| 6,835,731 | B2 | 12/2004 | Bridger et al. | |
| 7,238,711 | B1 * | 7/2007 | Grainger et al. | 514/323 |
| 2005/0154005 | A1 * | 7/2005 | Bridger et al. | 514/291 |
| 2005/0277670 | A1 | 12/2005 | Zhou et al. | |

FOREIGN PATENT DOCUMENTS

WO 2004/087068 * 10/2004

OTHER PUBLICATIONS

Gupta et al. (Immunol. Letters 78:29-34 (2001).*
Burger et al. (Blood 94(11):3658-3667 (Dec. 1, 1999).*
Shen et al. (Exp. Hematol. 29:1439-1447 (2001).*
Dummer Curr. Opin. Investig. Drugs 2(6):844-848 (2001).*
BioSpace Beat Dec. 8, 2003).*
Hussein (Expert. Opin. Pharmacother. 7(6):767-781 (2006)).*
Yeh et al. (Eur. J. Cancer 42:1554-1563 (2006)).*
Seaver (1994; Genetic Engineering vol. 14(14):pp. 10 and 21).*
Voskoglou-Nomikos (Clin. Can. Res. 9:4227-4239 (2003)).*
Dennis (Nature 442:739-741 (2006)).*
ExactAntigen website, "CXCR4 antibody" (pp. 1-3; Nov. 3, 2008).*
prosci-inc.com website, "CXCR4 antibody" (pp. 1-2; Nov. 3, 2008).*
ebioscience.com website, "anti-human CXCR4" (pp. 1-2, Nov. 3, 2008).*
abcam.com website, "CXCR4 antibodies" (p. 1; Nov. 3, 2008).*
Sachpatzidiz et al. (J. Biol. Chem. 278(2): 896-907 (2003).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Stein (Stein, C.A., Pharmacology and Therapeutics 85: 231-236, 2000).*
Stein, C.A., J. Clinical Investigation 108(5): 641-644, 2001).*
Caplen, N. J., August, Gene Therapy 11(16): 1241-1248, 2004.*
Lopez-Giral et al. (J. Leukocyte Biol. 76:462-471 (Aug. 2004)).*
RNDSystems Antibody Reference Guide (CXCR4 antibody, pp. 1-2), (Oct. 10, 2007).*
Wikipedia definition for monoclonal antibody (pp. 1-4) (May 14, 2008).*
Wikipedia definition for polyclonal antibodiy (pp. 1-4), (May 14, 2008).*
Cespdes et al. (Clin. Transl. Oncol. 8(5):318-329 (2006)).*
Talmadge et al. (Am. J. Pathol 170(3):793-804 (2007)).*
clinicaltrials.gov website (list of trials for AMD3100 and myeloma) pp. 1-3 (Oct. 6, 2008).*
Devine et al. (J. Clin. Oncol. 22(6):1095-1102 (Mar. 15, 2004)).*
Liles et al. (ref. 49 (Blood 102:2728-2730 (2003)).*
Finer et al., "*kat*: A High-Efficiency Retroviral Transduction System for Primary Human T Lymphocytes", *Blood*, 83(1):43-50 (1994).
Hideshima et al., "Novel Therapeutic Approaches for Multiple Myeloma", *Immunological Reviews*, 194, (2003),164-176.
Li et al., "The P190, P210, and P230 Forms of the *BCR/ABL* Oncogene Induce a Similar Chronic Myeloid Leukemia-like Syndrome in Mice but Have Different Lymphoid Leukemogenic Activity", J. Exp. Med., 189(9):1399-1412 (1999).
Moller et al., "Expression and Function of Chemokine Receptors in Human Multiple Myeloma", *Leukemia*, 17. (2003),203-210.
Burger, et al., "Chronic Lymphocytic Leukemia B Cells Express Functional CXCR4 Chemokine Receptors That Mediate Spontaneous Migration Beneath Bone Marrow Stromal Cells", *Blood*, 94(11),(1999),3658-3667.
Doench, et al., "siRNAs can function as miRNAs" *Genes & Development*, 17,(2003),438-442.
Gupta, et al., "Pharmacological evidence for complex and multiple site interaction of CXCR4 with SDF-1x: implications for development of selective CXCR4 antagonists", *Immunology Letters*, 78,(2001),29-34.
Shen, et al., "The Chemokine Receptor CXCR4 enhances integrin-mediated in vitro adhesion and facilitates engraftment of leukemic precursor-B cells in bone marrow", *Exp. Hematology*, 2, (2001),1439-1447.

* cited by examiner

*Primary Examiner*—Lynn Bristol
(74) *Attorney, Agent, or Firm*—Rissman Hendricks & Oliverio, LLP

(57) ABSTRACT

Methods for treating multiple myeloma with inhibitors of CXCR4 are described. The decreased expression of CXCR4 on multiple myeloma cells according to the invention results in decreased homing of the cells to the bone marrow and a reduction in the development of the disease. Also disclosed are pharmaceutical compositions incorporating such inhibitors for use in the therapeutic treatment of multiple myeloma. The treatment methods described herein can be used independently, or in conjunction with, other therapies for the treatment of multiple myeloma.

4 Claims, 5 Drawing Sheets

METHODS FOR THE TREATMENT OF MULTIPLE MYELOMA

CROSS-REFERENCE TO RELATED APPLICATIONS

This application claims the benefit of priority from U.S. Provisional Application No. 60/674,463, filed on Apr. 25, 2005, the specification of which is incorporated herein by reference.

GOVERNMENT SPONSORED RESEARCH OR DEVELOPMENT

This work was funded in whole or in part by a grant from the National Institutes of Health pursuant to Grant No. HL56949. The federal government may have certain rights in the invention.

BACKGROUND OF THE INVENTION

This invention relates to methods for the treatment of hematological malignancies that may reside in the bone marrow, particularly malignancies implicated by the expression of the CXCR4 receptor, such as multiple myeloma, using inhibitors of CXCR4. CXCR4 is known to be the receptor for the chemokine SDF-1α/CXCL 12. The preferred inhibitors of this invention are those which interfere with or block the CXCR4/SDF signaling pathway in humans.

The CXCR4 receptor is typically found on hematopoietic cells that reside in the bone marrow, such as white blood cells. The CXCR4 receptor is also expressed on human multiple myeloma cells and mouse multiple myeloma cells, i.e. cells isolated from mice that spontaneously develop multiple myeloma, as well as a variety of other cell types, such as stem cells. The expression of the CXCR4 receptor on these cells is believed to be a factor in their migration to the bone marrow, and for their retention in the bone marrow, and for regulating the trafficking and homing of cells involved in the immune system.

In humans and mice, multiple myeloma cells grow preferentialy in the bone marrow. These cells enter the bloodstream from their point of origin (typically a lymphoid tissue or the bone marrow itself). The cells infiltrate the bone marrow in previously unaffected bones until the bone marrow in all bones of the body become involved. The specific mechanism that allows these multiple myeloma cells to traffic from the blood to the bone marrow has not been elucidated as yet. See C. Moller et al., *Leukemia*, 17, pages 203-210 (2003).

Multiple myeloma is a form of cancer known to affect approximately 50,000 patients in the United States, with approximately 15,000 new patients diagnosed annually. Multiple myeloma is a hematological malignancy characterized by the clonal proliferation and accumulation of immunoglobulin-producing plasma B cells in bone marrow, causing the progressive destruction of bone tissue and bone marrow. If left untreated, the condition ultimately leads to the death of the patient.

Current treatments for mutiple myeloma center on the therapeutic use of various alkylating agents, anthracyclines and corticosteroids. These treatments typically do not cure the disease, but can effectively extend the life of the pateint for 3-4 years on average. Novel therpaies have also been proposed to target not only multiple myeloma clls, but also multiple myeloma/host cell interactions, as well as the bone marrow itself. These newer therapies target mechanisms whereby multiple myeloma cells grow and survive in the bone marrow, and utilize drugs such as thalidomide, thalidomide derivatives, and proteasome inhibitors. See T. Hideshima et al., *Immunological Reviews*, 194, pages 164-176 (2003).

A drug developed by AnorMed, Inc, designated as AMD3100, originally developed as an HIV therapeutic, has been evaluated in clinical trials for mobilizing stem cells that can be ultimately used in indications such as multiple myeloma. AMD3100 is described as a stem cell mobilizer that triggers the rapid movement of stem cells out of the bone marrow and into circulating blood by blocking the cellular receptor CXCR4. Once in the criculating blood of a subject, the stem cells can be collected for use in stem cell transplants in an attempt to restore the immune systenm of cancer patients who have had other treatments that previously destroyed immune cells. Typical drugs of this general description are disclosed in U.S. Pat. No. 6,825,351, issued Nov. 30, 2004, and U.S. Pat. No. 6,835,731, issued Dec. 28, 2004, the respective disclosures of which are incorporated herein in their entireties.

In spite of all the recent advances made in multiple myeloma treament, the disease remains largely incurable due, in part, to the development of tumor cell resistance to conventional therapies. Accordingly, there is currently no known cure for the disease.

It is therefore an objective of this invention to provide methods for the treatment of multiple myeloma, and other hematological malignancies that are associated with the bone marrow, using therapeutic treatments which are effective and are not impeded by drug resistance. It is a further objective of this invention to provide methods for the treatment of multiple myeloma utilizing therapies directed to interrupting the CXCR4/SDF signaling pathway of multiple myeloma cells in patients.

SUMMARY OF THE INVENTION

According to the present invention, a method for treating a hemtological malignancy in a mammal is provided comprising administering to the mammal an effective amount of a CXCR4 inhibitor. The CXCR4 inhibitor disrupts or impedes the CXCR4 binding to the chemokine SDF-1α/CXCL12. The inhibitor is administered to the mammal in need of such treatment as a pharmaceutical composition in amounts effective to interrupt the CXCR4-SDF pathway and to treat this disease. SDF-1α/CXCR4 signaling is active in the majority of cancer cells, including chronic lymphoid leukemia (CLL), chronic myeloid leukemia (CML), acute myelogenous leukemia (AML), acute lymphoblastic leukemia (ALL), and non-Hodgkin's lymphoma (NHL). In addition, this signaling pathway is also active in solid tumors, such as rhabdomyosarcoma, prostate cancer and melanoma. Breast and lung cancers are known to metastasize to the bone marrow, using the SDF-1α/CXCR4 pathway in the process.

In one embodiment, the CXCR4 chemokine receptor is on a multiple myeloma cell located in the bone marrow of a patient. The inhibitor is part of a pharmaceutical composition, along with other additives, and the composition is targeted to the bone marrow to impede or prevent the spread of the disease. Suitable inhibitors include antibodies to CXCR4, preferably monoclonal antibodies, small molecules, siRNA molecules, and dominant negative inhibitors.

In another embodiment, the invention is a pharmaceutical composition targeted to the bone marrow. The pharmaceutical composition includes a phsyiologically acceptable carrier and an adjuvant. The pharmaceutical compositon can be used indepentantly of other therapeutic compositions, or in combination with such other therapeutics.

The various features and advantages of the present invention will be better understood from the following specification when read in conjunction with the accompanying drawings.

DETAILED DESCRIPTION OF THE INVENTION

Figure 1:
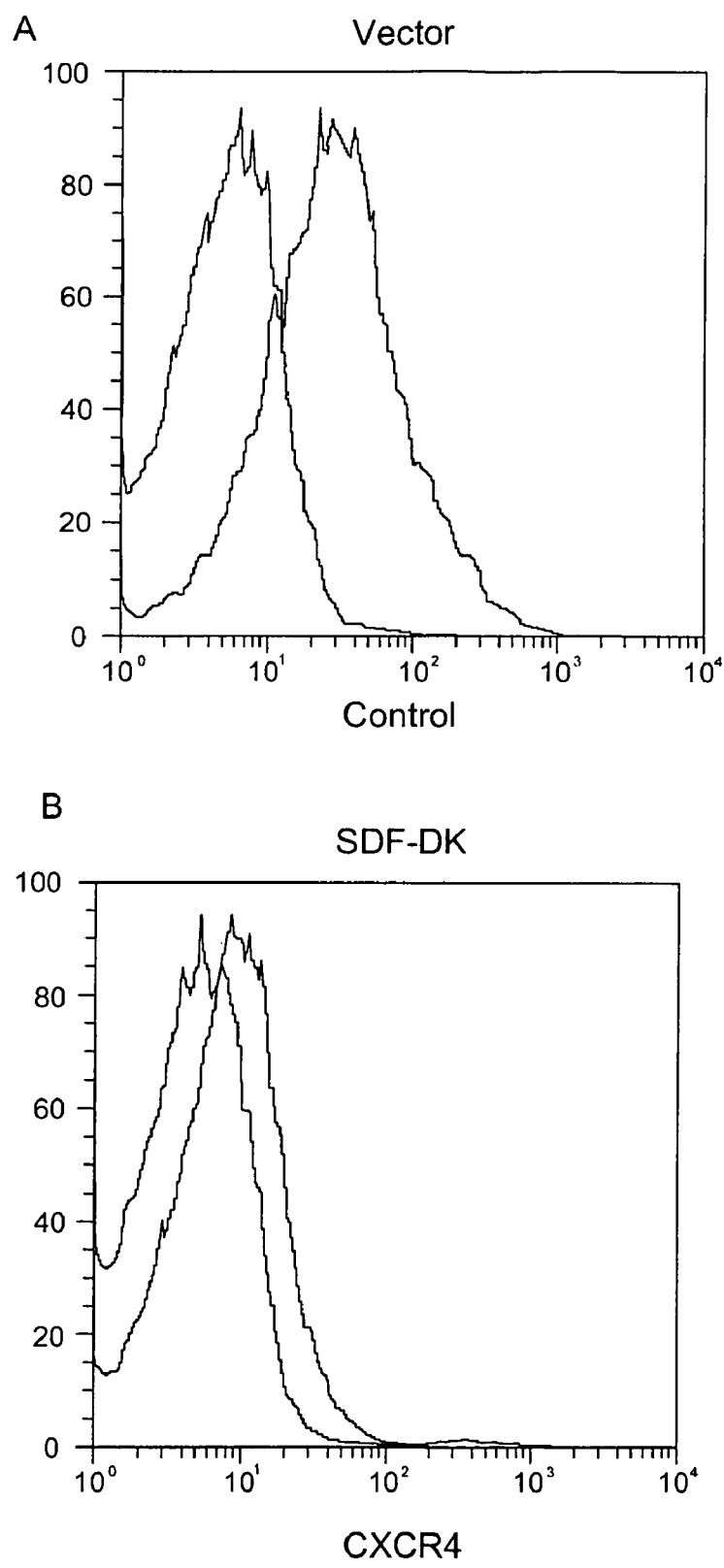
FIGS. 1A-1B are graphs illustrating the expression of CXCR4 on (FIG. 1A) vector 5T33MM mouse cells and (FIG. 1B) SDF-1αdegrakine (SDF-DK) 5T33MM cells. In the Figures, the red lines indicate the staining levels with control antibodies, and the blue lines indicate the presence of staining with a CXCR4 antibody.

This invention provides a method for treating multiple myeloma and other hematological malignancies of the bone marrow which involve the expression of the CXCR4 receptor by affected cells. The invention also provides a method for treating medical disorders by interrupting the CXCR4/SDF signaling pathway in the bone marrow cells of a mammal.

As used herein, the following terms and phrases shall have the following meanings unless indicated otherwise.

A "subject", as used herein, includes mammals such as human and non-human mammals. Preferred non-human mammals include primates, pigs, rodents, rabbits, canines, felines, sheep, horses, and goats. Veterinary applications are deemed within the scope of the present invention.

The abbreviations "MM" and "BM", as occasionally used herein, designate multiple myeloma and bone marrow, respectively.

The terms "treatment" or "treating" a medical condition, such as multiple myeloma or other hematological malignancies of the bone marrow, are intended to include both prophylactic and therapeutic methods of treating a subject. "Treatment" generally denotes the administration of a therapeutic agent to a subject having a disease or disorder, a symptom of a disease or disorder, or a predisposition toward a disease or disorder, for the purpose of preventing, alleviating, relieving, reducing the symptoms of, altering, or improving the medical condition or disorder. The methods of treatment described herein may be specifically modified or tailored based on a specific knowledge of the subject obtained by pharmacogenomics, and other methods for analyzing individual drug responses to therapies.

By "vaccine" is meant a prophylactic compostion intended to be used for the suppression, treatment or prevention of a disease. Vaccines can be administered orally, intravenously, nasally or subcutaneously.

An "inhibitor" in the context of the invention generally denotes an agent that can inhibit the interaction between the CXCR4 chemokine receptor and its ligand, and particularly the chemokine SDF-1α/CXCL12 ("SDF"). By "inhibiting" an interaction is generally meant, in the context of this invention, that the CXCR4 receptor and SDF chemokine are unable to properly bind to each such that the signaling pathway is interrupted. Such inhibition can result from a variety of events, such as by interrupting, preventing or reducing the binding of the chemokine to the receptor, inactivating the receptor or the chemokine, such as by cleavage or other modification, altering the affinity of the receptor and chemokine for each other, preventing or reducing the expression of the CXCR4 receptor on a cell, expressing an abnormal or inactive CXCR4 receptor, deactivating the CXCR4 receptor, preventing or reducing the proper conformational folding of the CXCR4 receptor, interfering with signals that are required to activate or deactivate the CXCR4 receptor or the SDF chemokine, or interfering with other molecules required for the normal synthesis or functioning of the receptor or chemokine.

Examples of types of inhibitors useful in the present invention are soluble forms of CXCR4 or SDF, inhibitory proteins, such as antibodies, inhibitory peptides and proteins, inhibitory carbohydrates, inhibitory glycoproteins, chemical entities, and small molecules.

A purified form of either CXCR4 or SDF, or a portion or fragment thereof, can compete with its cognate molecule for the binding site on the complementary molecule, and thereby reduce or eliminate binding between the CXCR4 receptor and the SDF chemokine. The soluble form can be obtained by natural or recombinant means, and is intended to include truncated forms and fragments.

Inhibitory proteins include anti-CXCR4 antibodies and anti-SDF antibodies, including humanized antibodies, chimeric antibodies, $Fab_2$ antibody fragments, polyclonal antibodies, and monoclonal antibodies. Monoclonal antibodies are preferred.

Inhibitory peptides include peptides or fragments of CXCR4 or SDF, which normally bind to CXCR4 so that the interaction or binding between CXCR4 and SDF is reduced or eliminated. The inhibitory peptides can recognize the binding site, or a portion of the binding site, of CXCR4.

Chemical entities and small molecules which are designed to interrupt the CXCR4/SDF pathway are also within the scope of the invention.

A "therapeutically effective amount" of a pharmaceutical composition means that amount which is capable of treating, or at least partially preventing or reversing the symptoms of, the medical condition or disease state. A therapeutically effective amount can be determined on an individual basis and is based, at least in part, on a consideration of the particular species of mammal, for example, the mammal's size, the particular inhibitor used, the type of delivery system used, and the time of administration relative to the progression of the disease. A therapeutically effective amount can be determined by one of ordinary skill in the art by employing such factors and using no more than routine experimentation.

Multiple myeloma can be characterized by a clonal proliferation and accumulation of immunogolbulin-producing plasma B cells in the bone marrow. Without intending to be bound by any particualar theory or mechanism of action, it is believed that malignant multiple myeloma cells may derive from B cells that have undergone antigen selection in the germinal center of secondary lymphoid organs. Such organs include the spleen and peripheral lymph nodes. To reach the bone marrow, multiple myeloma cells are also believed to home to the bone marrow using a multi-step molecular pathway, in a manner analogous to that of other leukocyte subtypes.

Blood-borne cells engage several sequential adhesion pathways to leave the circulatory system and lodge in a target organ. The initial steps of tethering and rolling are mediated by primary adhesion molecules, such as selectins or α4 integrins. This initial interaction does not require specific activation signals. To stop rolling and arrest, cells must engage secondary receptors, represented by the integrin family (β2 or α4), which must be activated to mediate firm adhesion. Integrin activation signals are frequently (but not always) provided by chemokines that are present on the endothelial cell surface. Most chemoattractant signals depend on Gαi-coupled (i.e. pertussis toxin (PTX)-sensitive) receptors. Activated integrins interact with endothelial immunoglobulin superfamily ligands. While some chemokines trigger intravascular adhesions, others direct migration of the family adherent leukocytes into and within the extravascular space. How adherent leukocytes "sense" chemokine gradients within a tissue and follow them to reach their end target is largely unknown.

Turning now to the Figures, FIGS. 1A-1B are a series of graphs showing the results achieved when 5T33MM cells are transduced with a control vector (FIG. 1A) or with an SDF-1α degrakine (FIG. 1B). In the Figures, a red line indicates the control antibody staining, and the blue line indicates the CXCR4 antibody staining.

FIGS. 2A-2E are a series of graphs illustrating the homing of 5T33MM cells to the bone marrow, and the survival/retention/proliferation of the 5T33MM cells at time intervals of 1 hour, 24 hours, 1 week, 2 weeks and 3 weeks after injection.

Figure 3:
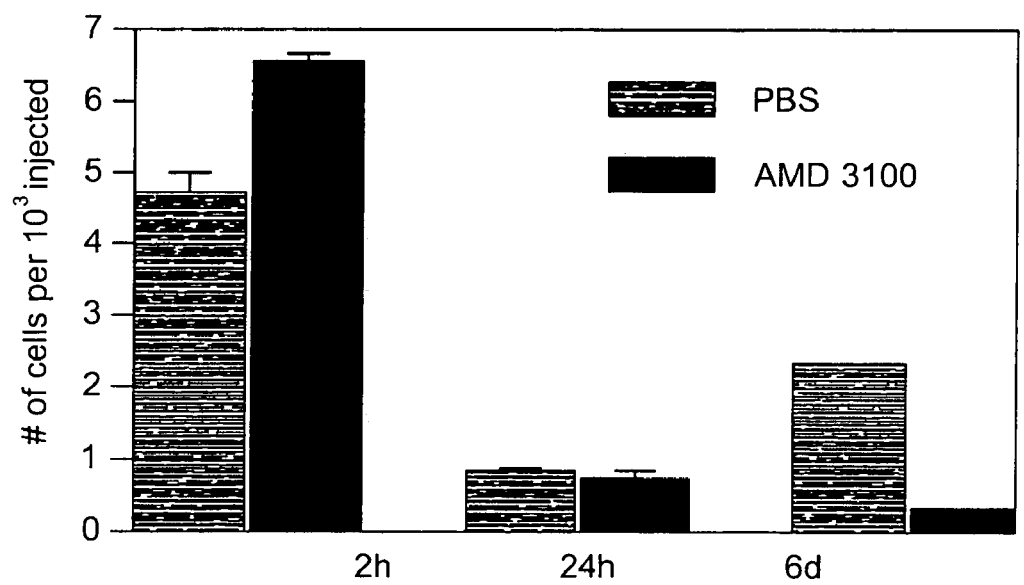
FIG. 3 is a graph demonstrating the role of CXCR4 in the homing/retention/proliferation/surviuval of 5T33MM cells when CXCR4-CXCL12 interaction is inhibited pharmacologically.

FIG. 3 is a graph demonstrating the homing/retention/proliferation/survival of 5T33MM cells when CXCR4-CXCL12 interaction is inhibited pharmacologically. AMD3100 and PBS is implanted, and the survival rate after 2 hours, 24 hours and 6 days is measured.

Figure 4:
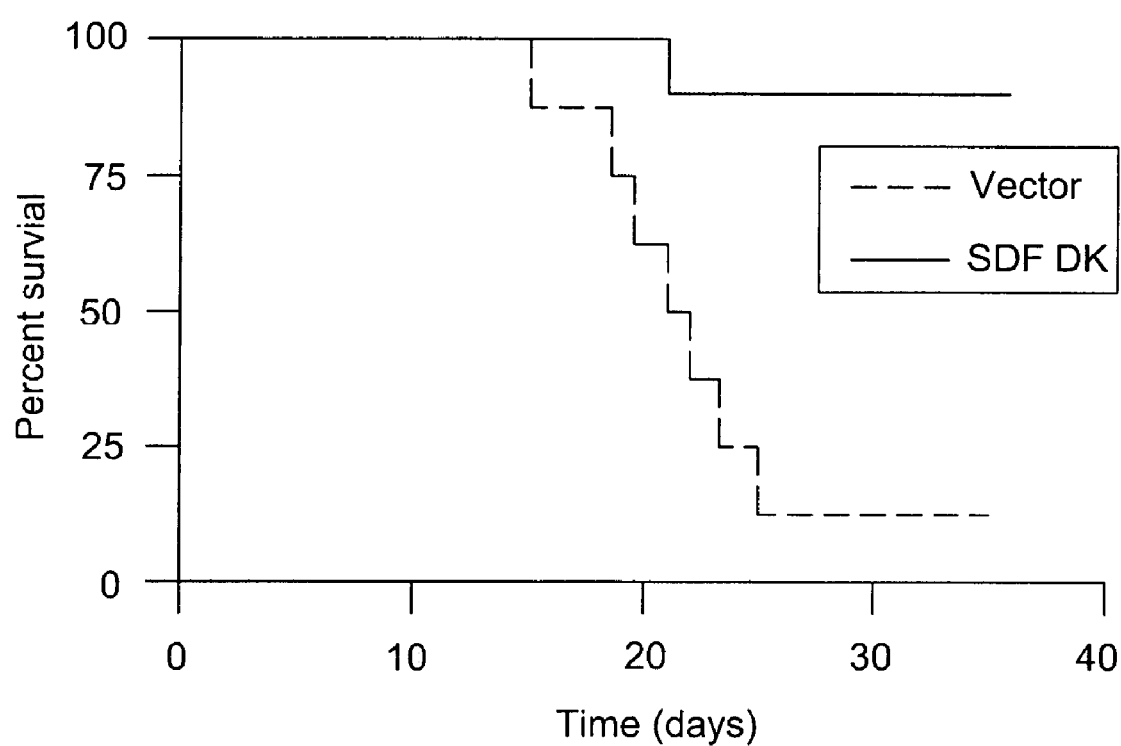
FIG. 4 is a graph illustrating the survival of mice injected with 5T33MM transduced with (a) a vector, or (b) SDF-1αdegrakine (SDF-DK) cells.

FIG. 4 is a graph illustrating the results on mice injected with 5T33MM cells transduced with a vector, and 5T33MM cells transduced with SDF-1α (SDF-DK) cells. The survival of the mice is measured using the Kaplan-Meier survival curve, P<0.0001 between the vector and SDF-DK by the log-rank test, wherein n=9 for the vector, and n=11 for SDF-DK.

Figure 5:
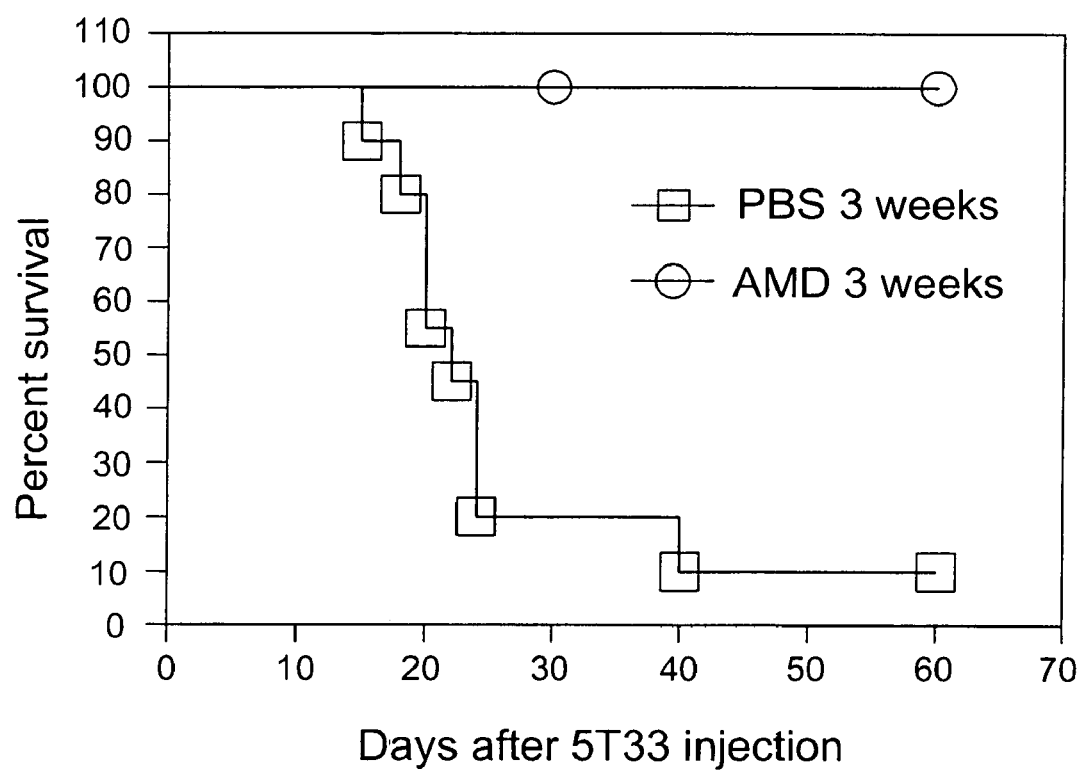
FIG. 5 is a graph illustrating the effects of AMD3100 and PBS administered to mice injected with $10 \times 10^6$ $5T33^{eGFP}$ cells.

FIG. 5 is a graph showing the survival of C57BL/6 mice after injection with $10 \times 10^6$ $5T33^{eGFP}$ cells. Osmotic pumps are installed at the time of injection, and either AMD3100 or PBS is implanted. The osmotic pumps are changed every 7 days, and the pump administration is discontinued after 21 days. The survival rate, P<0.05, is measured between PBS and AMD3100 by the log-rank test, n=3.

The CXCR4 inhibitors of this invention can be incorporated into pharmaceutical compositions suitable for administration to a subject. Such compositions typically comprise the inhibitor and a pharmaceutically acceptable carrier. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media, and agents for pharmaceutically active substances is well known in the art. Except insofar as any conventional media or agent is incompatible with the active compound, the use thereof in the pharmaceutical compositions of the invention is contemplated. Supplementary active compounds can also be incorporated into the present compositions.

The administration of the active compounds (CXCR4 inhibitors) of the invention may be for either a prophylactic or therapeutic purpose. Accordingly, in one embodiment, a "therapeutically effective dose" refers to that amount of inhibitor sufficient to result in a detectable change in the physiology of a recipient patient. In another embodiment, a "therapeutically effective dose" refers to an amount of inhibitor sufficient to result in modulation of the CXCR4/SDF pathway. In yet another embodiment, a "therapeutically effective dose" refers to an amount of inhibitor sufficient to result in the amelioration of symptoms of multiple myeloma. In still another embodiment, a "therapeutically effective dose" refers to an amount of inhibitor sufficient to prevent the occurrence of multiple myeloma in a patient.

Toxicity and therapeutic efficacy of the inhibitory compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of the affected tissue, i.e. the bone marrow in most instances, in order to minimize potential damage to uninfected cells, and thereby to reduce side effects.

Data obtained from cell culture assays and animal studies can be used in formulating a range of dosages for use in humans. The dosage of such compounds lies preferably within a range of circulation concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Generally, the therapeutically effective amount of the pharmaceutical compositions used herein will vary with the age of the subject and condition, as well as the nature and extent of the disease, all of which can be determined by one of ordinary skill in the art. The dosage may be adjusted by the physician, particularly in the event of any complication. A therapeutically effective amount will typically vary from 0.01 mg/kg to about 1000 mg/kg, preferably from about 0.1 mg/kg to about 200 mg/kg, and most preferably from about 0.2 mg/kg to about 20 mg/kg.

The present invention encompasses active agents which modulate or inhibit CXCR4 activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecules depend upon a number of factors within the knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator or inhibitor of CXCR4 activity is administered in combination with other agents (e.g., a small molecule), or in conjunction with another, complementary treatment regime. Accordingly, the subject may be treated, for example with a CXCR4 inhibitor, and further treated with another anti-cancer agent.

The pharmaceutical compositions can be included in a container, pack, or dispenser together with instructions for administration.

The pharmaceutical composition of the invention can include any pharmaceutically acceptable carrier known in the art. Further, the composition can include any adjuvant known in the art, e.g., Freund's complete or incomplete adjuvant. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcohol/aqueous solutions, emulsions or suspensions, including saline and buffered media. Parenteral vehicles include sodium chloride solution, Ringer's dextrose, xylitol, dextrose and sodium chloride, lactated Ringer's solution or fixed oils. Intravenous vehicles include fluid and nutrient replenishers, electrolyte replenishers (such as those based on Ringer's dextrose or xylitol), and the like. Preservatives and other additives may also be present such as, for example, antimicrobials, antioxidants, chelating agents, inert gases and the like.

The pharmaceutical compositions can be administered to the mammal by any method which allows the CXCR4 inhibitor to reach the appropriate bone marrow tissue or cells. These methods include, e.g., injection, infusion, deposition, implantation, oral ingestion, topical administration, or any combination thereof. Injections can be, e.g., by intravenous, intramuscular, intradermal, subcutaneous or intraperitoneal administration. Single or multiple doses can be administered over a given time period, depending upon the progression of the disease, as can be determined by one skilled in the art without undue experimentation. Administration can be alone or in combination with other therapeutic agents. The route of administration will depend on the composition of a particular therapeutic preparation of the invention, and on the intended site of action. The present compositions can be delivered directly to the site of action.

Other delivery systems can include time-release, delayed release or sustained release delivery systems. Such systems can avoid repeated administrations of the active compounds of the invention, thereby increasing the convenience to the subject and the physician. Many types of delayed release delivery systems are available and known to those of ordinary skill in the art. These include polymer-based systems such as polylactic and polyglycolic acid, polyanhydrides and polycaprolactone; nonpolymer systems include lipids such as sterols, and particularly cholesterol, cholesterol esters and fatty acids or neutral fats such as mono-, di- and triglycerides; hydrogel release systems; silastic systems; peptide based systems; wax coatings, compressed tablets using conventional binders and excipients, partially fused implants and the like. In addition, pump-based hardware delivery systems can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 clays. Long-term sustained release implants are well known to those of ordinary skill in the art and include some of the release systems described above.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Pharmacogenomics thereby allows a clinician or physician to target prophylactic or therapeutic treatments to patients who will most benefit from the treatment and to avoid treatment of patients who will experience toxic drug-related side effects.

This invention is further illustrated by the following examples which should not be construed as limiting. The contents of all references, patents and published patent applications cited throughout this application, are incorporated herein by reference.

In the following examples, a mouse model of multiple myeloma is used. The murine model of is the 5T33MM model, which originated from a spontaneous case of multiple myeloma in aged mice of the C57BL/KaiwRij strain (Radl et al, 1979). The 5T33MM model is initiated and maintained by transplanting multiple myeloma-affected bone marrow into young syngenic mouse recipients. The clinical characteristics of this mouse model are similar to human multiple myeloma, which makes it a valuable tool to study multiple myeloma.

EXAMPLE 1

Maintenance of 5T33MM Cells

5T33MM cells can be maintained both in vivo and in vitro. For in vivo maintenance, the bone marrow of sick mice is isolated by flushing long bones (femora and tibia) with sterile phosphate buffered saline (PBS). Flushing is performed with a syringe through a 21G needle. After isolation, red blood cells are lysed and a single cell suspension is prepared. These cells are injected in a secondary recipient, which develops the disease within a certain time period. The time for multiple myeloma development depends on the number of cells injected. For in vitro maintenance, 5T33MM cells are cultured in a special media, which includes RPMI-1640, 10% fetal calf serum (FCS), L-glutarnine, penicillin and streptomycin, sodium pyruvate, non-essential amino acids, and β-mercaptoethanol. Cells are seeded in a culture flask, and media is changed once in three days. Injection of the in vitro cultured cells mediates disease development in recipient mice within 2-4 weeks, depending on the number of cells injected. In results shown, we only used in vitro cultured RT33MM cells.

EXAMPLE 2

CXCR4 Expression in Mouse 5T33MM Cells

Cells that home to the bone marrow typically utilize signals from the chemokine receptor CXCR4 to undergo integrin mediated arrest. 5T33MM cells express CXCR4, and it is hypothesized that the development of multiple myeloma can be disrupted by interfering with cell signaling through the CXCR4 receptor. Accordingly, a virus that expresses the SDF1α degrakine is transduced into 5T33MM cells to reduce the expression of CXCR4 using retroviral technology.

The production of the retrovirus is performed as described in Li et al., *J. Exp. Med.*, 189, pages 1399-1512 (1999), the disclosure of which is incorporated by reference herein in its entirety. 10 μg of retroviral vector DNA and 5 μg of MCV-ecopac, an ecotropic single-genome packaging construct, are tranfected as per a 6-cm dish of HEK-293T as described in Finer et al., *Blood*, 83, pages 43-50 (1994). The medium is changed at 24 hours, and a virus supernatant is harvested at 48 hours after transfection. The supernatant is passed through a 0.45-μm filter, aliquoted, and frozen at 80° C. 5T33 cells are transduced with a retrovirus to improve the transduction efficiency (Kotani et al., *Human Gene Therapy*, 5, pages 19-28 (1994)). $1 \times 10^6$ 5T33 cells and viral supernatant are co-centrifuged at 700×g for 24 hours, and then moved to a 37° C. incubator. Transduction efficiency is assayed by FACS measurement of fluorescent reporter genes (eGFP and DsRed). Transduced 5T33 cells are FACS sorted (FACS Aria, B&D) to obtain homogeneous eGFP$^+$ or DsRed$^+$ populations of cells.

As shown in FIG. 1A, the vector-transduced cells express CXCR4, while FIG. 1B shows that degrakine transduced cells express 60% less CXCR4.

EXAMPLE 3

Bone Marrow Homing of Mouse 5T33MM Cells

Figure 2:
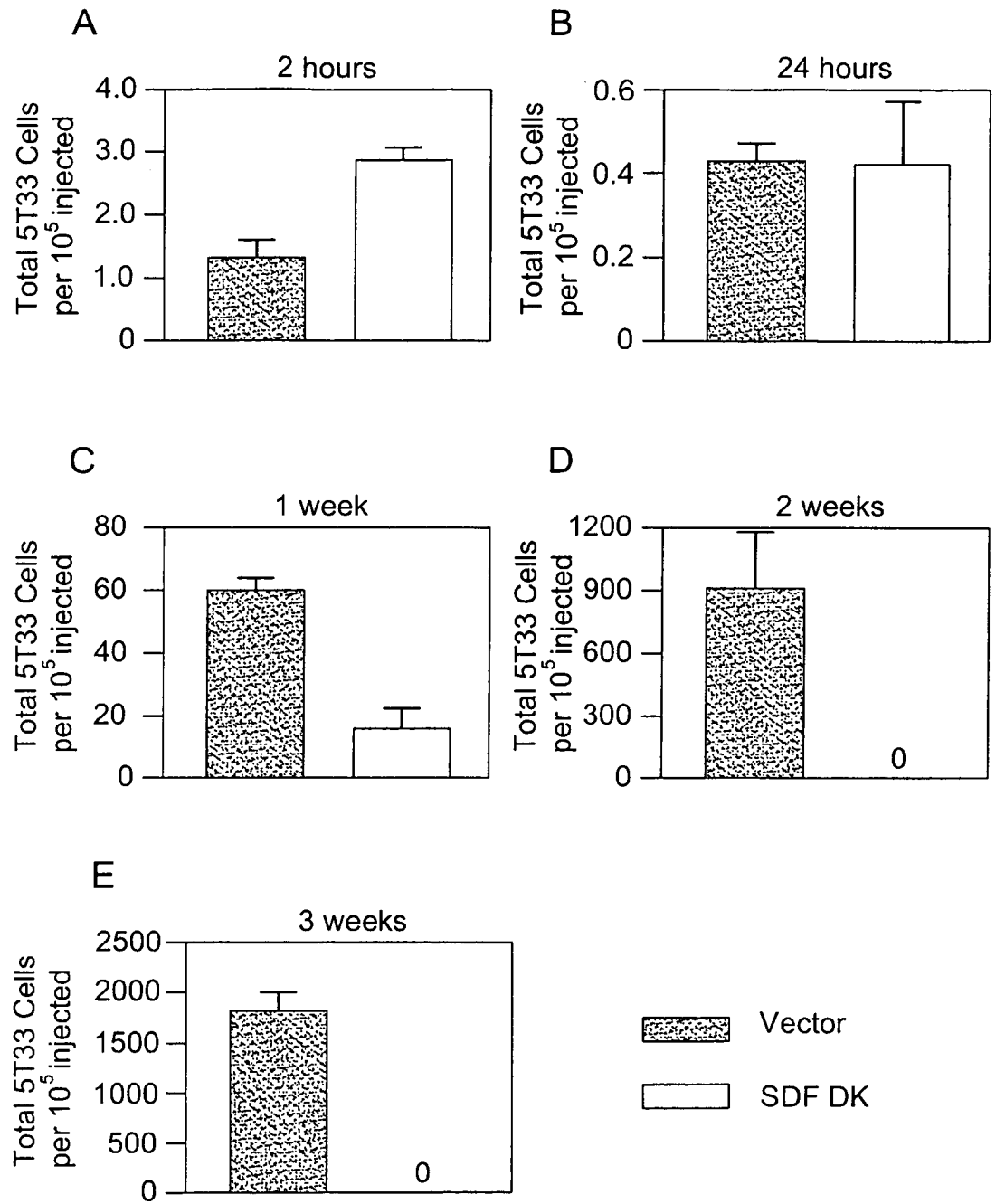
FIGS. 2A-2E are graphs illustrating the homing/retention/proliferation/survival of control 5T33MM cells and cells which are genetically modified to prevent surface CXCR4 expression in bone marrow.

5T33MM cells, obtained as described above, are injected into recipient mice. While homing (2 hours) and retention (24 hours) does not depend on CXCR4 expression, later events, such as cell proliferation and/or survival (1 to 3 weeks) are decreased in the absence of CXCR4 (FIG. 2).

Similar results are obtained when 5T33MM cells are manipulated pharmaceutically instead of genetically: when recepients are treated with the CXCR4 inhibitor AMD3100, it does not affect the homing (2 hours) or retention (24 hours) of the 5T33MM cells, but it significantly reduces their proliferation/survival (6 days) (FIG. 3).

EXAMPLE 4

Vector 5T33MM cells and SDF-1α Degrakine cells and Treatment of Multiple Myeloma with AMD3100.

Following the injection of $10 \times 10^6$ 5T33$^{vector}$ or 5T33$^{SDF-DK}$ cells, mice that received 5T33$^{SDF-DK}$ cells displayed dramatically increased survival compared to mice injected with 5T33$^{vector}$ cells. See FIG. 4.

When AMD3100 is administered at the time 5T33 cells are injected, an increase in survival is observed. AMD3100 is delivered via a subcutaneous osmotic pump at a concentration of 25 mg/mL and a delivery rate of 0.5 μl/hr. The osmotic devices delivered the drug for 21 days. See FIG. 5.

Table 1 below shows the survival and serum IgG$_{2b}$ levels of mice which were given 5T33 MM cells. The mice were transduced with a control vector, the SDF1α degradine, or with twice the levels of the SDF1α degradine vector. Mice that received trasnduced 5T33MM cells experienced a reduction in mortality as compare to the control mice. Mice that survived longer than 40 days were considered free of the disease. In humans, multiple myeloma is associated with increased levels of serum immunogobulin. Mice that did not develop multiple myeloma do not have increased levels of IgG$_{2b}$ paraprotein, while mice with multiple myeloma had elevated IgG$_{2b}$ levels.

TABLE 1

|  | Survival (days post 5T33 injection) | Serum IgG$_{2b}$ Levels (mg/mL) |
|---|---|---|
| Vector 1 | >40 | 3.8 |
| Vector 2 | 25 | 8.8 |
| Vector 3 | 19 | 9.9 |
| Vector 4 | 21 | 4.4 |
| Vector 5 | 21 | 4.5 |
| SDF1α Degrakine 1 | >40 | 2.7 |
| SDF1α Degrakine 2 | >40 | 3.2 |
| SDF1α Degrakine 3 | >40 | 1.6 |

The above examples demonstrate, inter alia, that the attenuation of CXCR4 expression in 5T33MM cells completely blocked the development of fatal multiple myeloma in recipient mice even when CXCR4 expression was only reduced to subnormal levels without achieving complete inhibition of the receptor or preventing homing to the bone marrow. Without wishing to be bound by any theory or mechanism of action, it is believed that a strong signal sent through the CXCR4 receptor is required for multiple myeloma development, not only for hematogenous dissemination, but also for the survival and/or proliferation of bone marrow-resistant tumor cells. Accordingly, it is concluded that interfering with the function of the CXCR4 receptor on multiple myeloma cells can serve as a method for treating multiple myeloma in humans.

A number of embodiments of the invention have been described herein. Nevertheless, it will be understood that various modifications may be made to the invention without departing from its spirit and scope. Accordingly, embodiments other than those specifically described herein are intended to be embraced by the following claims. Those skilled in the art will be able to ascertain, using no more than routine experimentation, many equivalents of the specific embodiments of the invention described herein. These and all other equivalents are intended to be encompassed by the following claims.

What is claimed is:

1. A method for treating a human subject having, or suspected of having, a multiple myeloma comprising administering in vivo to the subject an effective amount of a pharmaceutical composition comprising AMD3100, said method being effective to interrupt the CXCR4/SDF signaling pathway in multiple myeloma cells in the bone marrow of said subject thereby limiting the development of multiple myeloma and increasing survivability of the subject, said composition being administered over a time period of about 21 days.

2. The method of claim 1 wherein the pharmaceutical composition includes a pharmaceutically acceptable carrier and an adjuvant.

3. The method of claim 1 which is used as an adjunct to another therapeutic treatment for multiple myeloma.

4. The method of claim 1 wherein the composition is administered using an osmotic pump.

* * * * *